(12) United States Patent
Kaigler, Sr.

(10) Patent No.: US 8,255,071 B2
(45) Date of Patent: Aug. 28, 2012

(54) METHOD AND SYSTEM FOR FORMING A DENTAL PROSTHESIS

(75) Inventor: Darnell Kaigler, Sr., Detroit, MI (US)

(73) Assignee: Innovative Health Technologies, LLC, Anchorage, AK (US)

( * ) Notice: Subject to any disclaimer, the term of this patent is extended or adjusted under 35 U.S.C. 154(b) by 405 days.

(21) Appl. No.: 12/270,520

(22) Filed: Nov. 13, 2008

(65) Prior Publication Data

US 2010/0119996 A1 May 13, 2010

(51) Int. Cl.
*G06F 19/00* (2011.01)
(52) U.S. Cl. ......................................... 700/119; 700/186
(58) Field of Classification Search .......... 700/119–120, 700/189, 186, 159; 264/19; 382/154; 345/204
See application file for complete search history.

(56) References Cited

U.S. PATENT DOCUMENTS

| | | | |
|---|---|---|---|
| 6,050,819 A * | 4/2000 | Robinson ...................... | 433/173 |
| 6,648,640 B2 | 11/2003 | Rubbert et al. | |
| 6,808,658 B2 * | 10/2004 | Stover ............................ | 264/1.6 |
| 6,808,659 B2 | 10/2004 | Schulman et al. | |
| 7,027,642 B2 * | 4/2006 | Rubbert et al. ............... | 382/154 |
| 7,233,323 B2 * | 6/2007 | Watsuda ....................... | 345/204 |
| 7,440,540 B2 * | 10/2008 | Kano .............................. | 378/41 |
| 7,698,014 B2 * | 4/2010 | Dunne et al. .................. | 700/118 |
| 2003/0055433 A1 * | 3/2003 | Krenkel et al. ................. | 606/86 |
| 2003/0096210 A1 | 5/2003 | Rubbert et al. | |
| 2003/0165795 A1 * | 9/2003 | Stucki-McCormick ...... | 433/173 |
| 2004/0133207 A1 * | 7/2004 | Abdou ............................ | 606/73 |
| 2007/0081718 A1 * | 4/2007 | Rubbert et al. ............... | 382/154 |
| 2007/0287131 A1 * | 12/2007 | Ruppert et al. ............... | 433/223 |
| 2008/0015727 A1 * | 1/2008 | Dunne et al. .................. | 700/118 |
| 2008/0131841 A1 | 6/2008 | Taub et al. | |

* cited by examiner

*Primary Examiner* — Kidest Bahta
(74) *Attorney, Agent, or Firm* — Dickstein Shapiro LLP

(57) ABSTRACT

A system and method for use in constructing a prosthesis/complete restoration that obtains a digital dentition model, such as a 3D geometric surface model or a 3D volumetric image model, processes the digital dentition model to form a virtual model, forms a virtual mold including a digital prosthesis and/or complete restoration, and uses the virtual model to construct the prosthesis/complete restoration. Processing circuitry, such as a programmed server, can be used to obtain the digital dentition model and form the virtual mold. A rapid manufacturing device can be used to construct the prosthesis/complete restoration.

17 Claims, 12 Drawing Sheets

METHOD AND SYSTEM FOR FORMING A DENTAL PROSTHESIS

FIELD OF THE INVENTION

Embodiments described herein relate generally to dental implant formation systems and methods, and more particularly, to computer-implemented dental implant systems and methods for forming prostheses/complete restorations using three-dimensional imagery.

BACKGROUND OF THE INVENTION

Many surgical procedures concern the temporary or permanent insertion, into the soft or bony tissue of a patient, of prosthetic and other artificial devices that are required to fit the anatomy of the patient to a very high degree of precision and accuracy. One such application concerns implant dentistry, in the course of which one or more implants are surgically placed within the jawbone of a patient, to receive and support prosthetics, e.g., complete restoration, designed to simulate and replace one or more natural teeth lost by the patient. It is well known that, to be wholly successful, implant procedures must adhere to very strict placement, orientation and sizing requirements determined by existing bone structure and dentition, whereby the prosthetics to be fitted onto surgically-placed implants must be preferably designed, shaped and sized specifically to conform to the precise anatomical geometry of the patient, including the location, shape and size of adjoining teeth, and must transition to the precise orientation of the principal axis of the supporting implant with a high degree of accuracy.

Conventional methods for meeting these rigorous requirements provide for the creation of a model of the patient's jaw and dentition, the making of a model comprising the taking of a so-called "impression" of the patient's dentition, using a malleable substance placed over and around the teeth in the patient's mouth comprising the entire dental arch. Typically this impression is taken following the surgical insertion of the implant. Typically, reference components called impression copings are affixed to the external extremity of the inserted implant, and serve to reference the location and angular orientation of the implants. Subsequently, a model made from a mold based on the impression will incorporate so-called "analog" implants to model the implants in the patient's jaw, and prosthetic devices for the implants will be designed and manufactured based on the geometry of the model created as described.

In actual practice the conventional procedure described above is fraught with numerous difficulties and shortcomings. It has proven impossible for dental practitioners to make dental impressions, and thus models, that are consistently free of dimensional and positional errors. In recent years, efforts have been made to employ image-based modeling techniques to address these well-known problems of conventional implant dentistry procedures. For example, two-dimensional (2D) and three-dimensional (3D) digital image technology has been tapped as a tool to assist in dental and orthodontic treatment. In these efforts, images are taken of the patient's mouth, and a three-dimensional image is used to assist in dental treatments. The particular demands for great accuracy, however, have thus far resulted in the absence of acceptable three-dimensional imaging techniques in the field of dentistry that can result in an accurately formed prosthesis and/or complete restoration.

BRIEF SUMMARY OF THE INVENTION

Embodiments described within relate to a three-dimensional-based modeling technique designed for dentistry and related medical applications to form prostheses/complete restorations. One technique for producing a prosthesis/complete restoration involves obtaining a digital dentition model; using the obtained digital dentition model to form a virtual model of a prosthesis and/or complete restoration; and using the virtual model to construct the prosthesis and/or complete restoration. Processing circuitry, such as a programmed computer, is used to obtain the digital dentition model and create the virtual model. A rapid manufacturing device, such as a stereolithography machine, is commonly used to construct the prosthesis/complete restoration. In some implementations, the processing circuitry receives a 3D surface model of the dentition and creates a volumetric image model from the 3D surface model. In other words, three-dimensional image processing software, preferably comprising algorithms, is then employed to interpret the 3D image data acquired by any scanning means and creates a virtual three dimensional model used to construct a prosthesis/complete restoration.

DETAILED DESCRIPTION OF THE INVENTION

Figure 1:
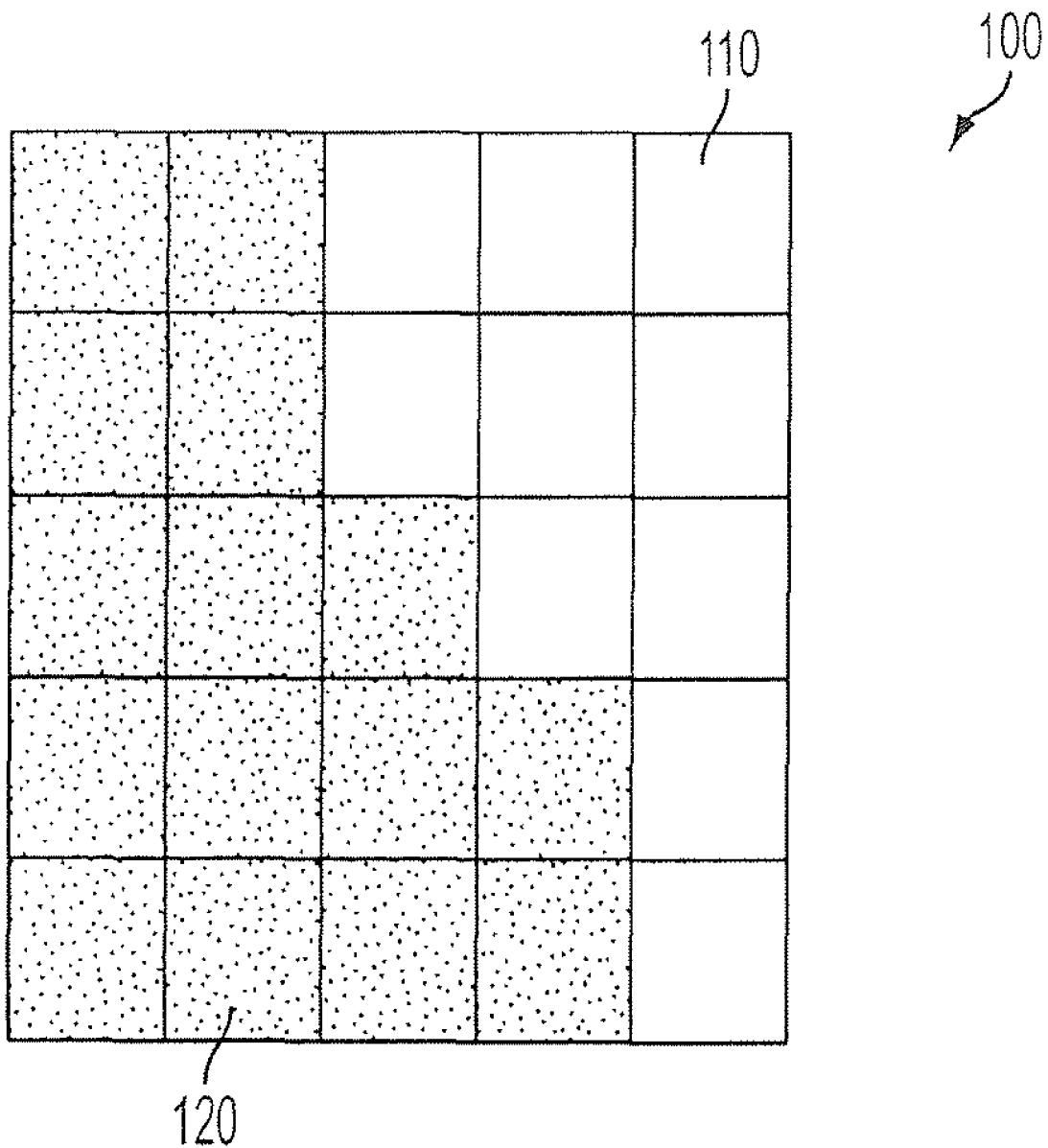
FIG. 1 is an illustration of a component of an embodiment described herein.

Embodiments discussed herein provide techniques and systems for producing prostheses. In the following detailed description, reference is made to the accompanying drawings which form a part hereof, and in which is shown by way of illustration specific embodiments that may be practiced. These embodiments are described in sufficient detail to enable those of ordinary skill in the art to make and use them, and it is to be understood that structural, logical, or procedural changes may be made to the specific embodiments disclosed.

In particular, the embodiments described herein relate to a method and system of producing a prosthesis/complete restoration comprising receiving a 3D digital data set that models individual portions of a patient's dentition, including individual teeth and gingival tissue surrounding the teeth, generating therefrom a virtual model, and deploying a virtual prosthesis/complete restoration to a rapid manufacturing device to construct the prosthesis/complete restoration. The embodiments also describe computer-implemented techniques for using the 3D digital data set in designing and producing the prosthesis/complete restoration for the patient.

One such technique involves receiving an initial 3D digital data set that represents the patient's teeth before treatment, including a specified desired treatment, i.e., client specifications, for the patient's teeth, and forming the necessary prosthetic that will cure the shortcomings of the patient's teeth. The initial 3D digital data set is often a voxel representation obtained by optically scanning a physical dentition model or the patient's teeth directly (described below) or obtained by other imaging technology.

The embodiments described herein are particularly suitable and intended for medical and dental applications, and are particularly suited for use in the field of implant dentistry and related applications. Dental implants, i.e., prostheses and/or complete restoration, are used to support the restoration of missing teeth. For example, implant fixtures are surgically implanted into a patient by a dentist. These dental implants typically will be "restored" with abutments and crowns; that is, following successful implantation of implant fixtures into the jaw of the patient, prostheses including abutments and crowns will be affixed to the implanted fixtures to provide the patient with a restoration of the patient's natural teeth. In an important aspect, the method and system described herein enable a designer/manufacturer/supplier of prostheses/complete restorations to accurately measure the location and orientation of the implants in relation to the surrounding oral environment, and thereby to design and construct the needed prosthetic that is, to a very high degree of precision and accuracy, customized to the anatomy and the existing dentition of the patient.

The embodiments enable the use of any 3D digital data capture means that produces a point cloud representing the three dimensional surface. Such data capture means may, for example, be a hand-held or frame-fixed three-dimensional laser scanner, an ordinary digital camera, an ultrasound X-ray machine, desktop scanner or any other imaging device that is practically suited to dental applications. Image-data capturing means usable with the embodiments described herein are readily available from commercial sources, and would for example include three-dimensional laser scanners of medical grade CT. In the practice of the embodiments, spatial information, i.e., 3D digital data, may be obtained directly using intra-oral scanning and then processed as described below. In the alternative, however, it should also be appreciated that the embodiments may be used in conjunction with the conventional practice whereby impressions are taken of the patient's dentition, and the dentition is replicated in the form of a master cast made from impressions.

FIG. 1 shows a partial slice 100 taken from an exemplary 3D digital data set (voxel representation) of a patient's dentition for use in prosthesis fabrication. Each image slice 100 in the voxel representation has a thickness of one voxel and includes both light-colored (e.g., white) voxels 110 and dark-colored (e.g., black) voxels 120. The light-colored voxels represent the patient's dentition, which in many cases replicates the patient's dentition at a selected treatment stage, and the dark-colored voxels represent the background image. The computer-implemented method for producing the virtual model and virtual prosthesis and/or complete restoration described herein analyzes each successive image slice 100 to identify the light-colored voxels and constructs the virtual model one layer at a time by creating a virtual surface at locations that correspond to the light-colored voxels.

Figure 2:
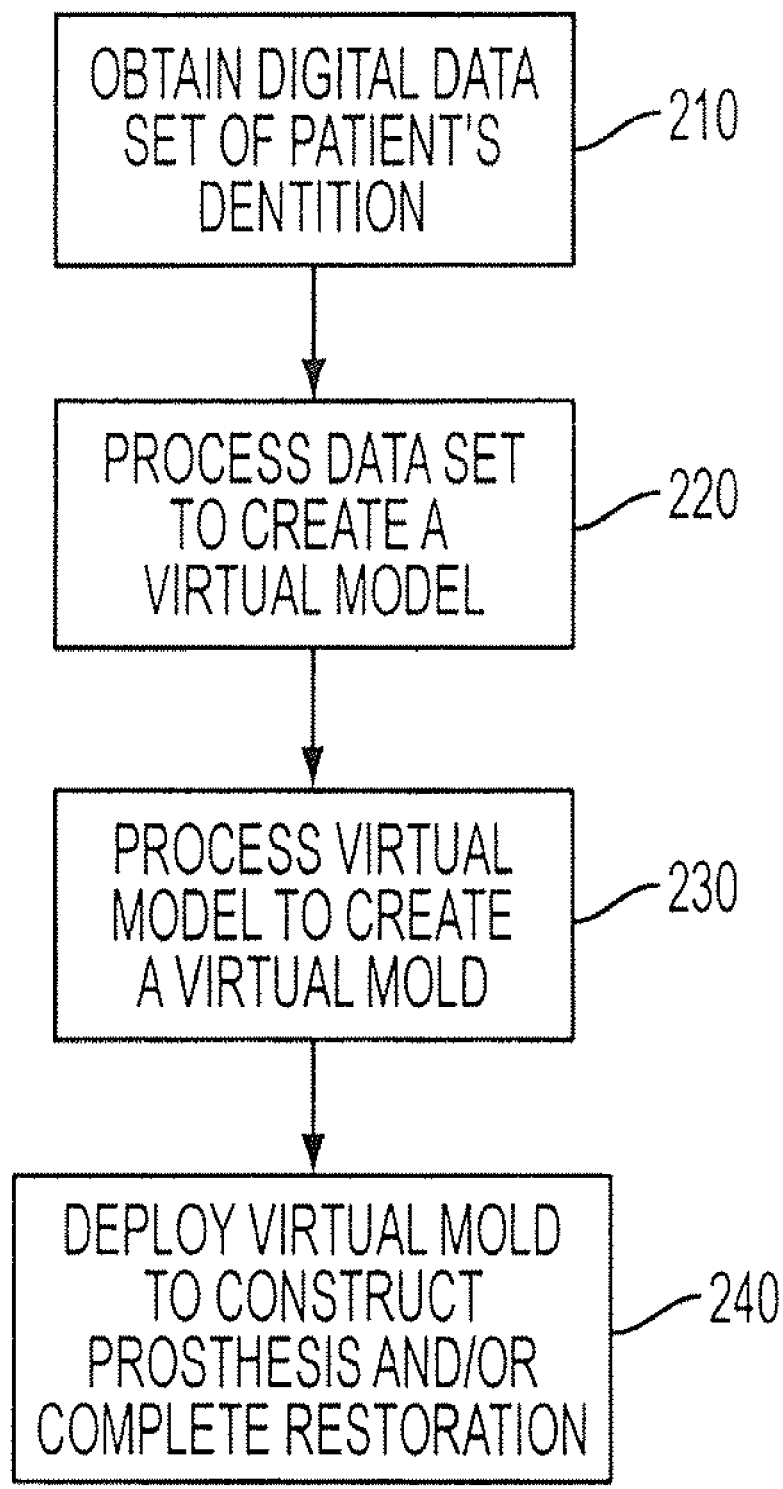
FIG. 2 is a flowchart of an embodiment described herein.

FIG. 2 illustrates an embodiment of a computer-implemented technique for producing the virtual prosthesis and/or complete restoration. In the technique, a server, i.e., a computer, first receives or creates a digital data set embodying a 3D digital data set, e.g., a model, of the patient's dentition (step 210). The server then processes the 3D digital data set to form a virtual model of the patient's dentition (step 220) and then forms a virtual mold, i.e., virtual prosthesis and/or complete restoration (step 230). Once a virtual mold is formed, the server deploys the created virtual mold to a rapid manufacturing device, such as a stereolithography machine or laser engineer net shaping machine, for use in constructing the actual, physical prosthesis and/or complete restoration (step 240). A rapid manufacturing system can be an additive manufacturing process that creates a model of an object directly from a CAD model (or other known model) by building it in layers (described below).

Figure 3:
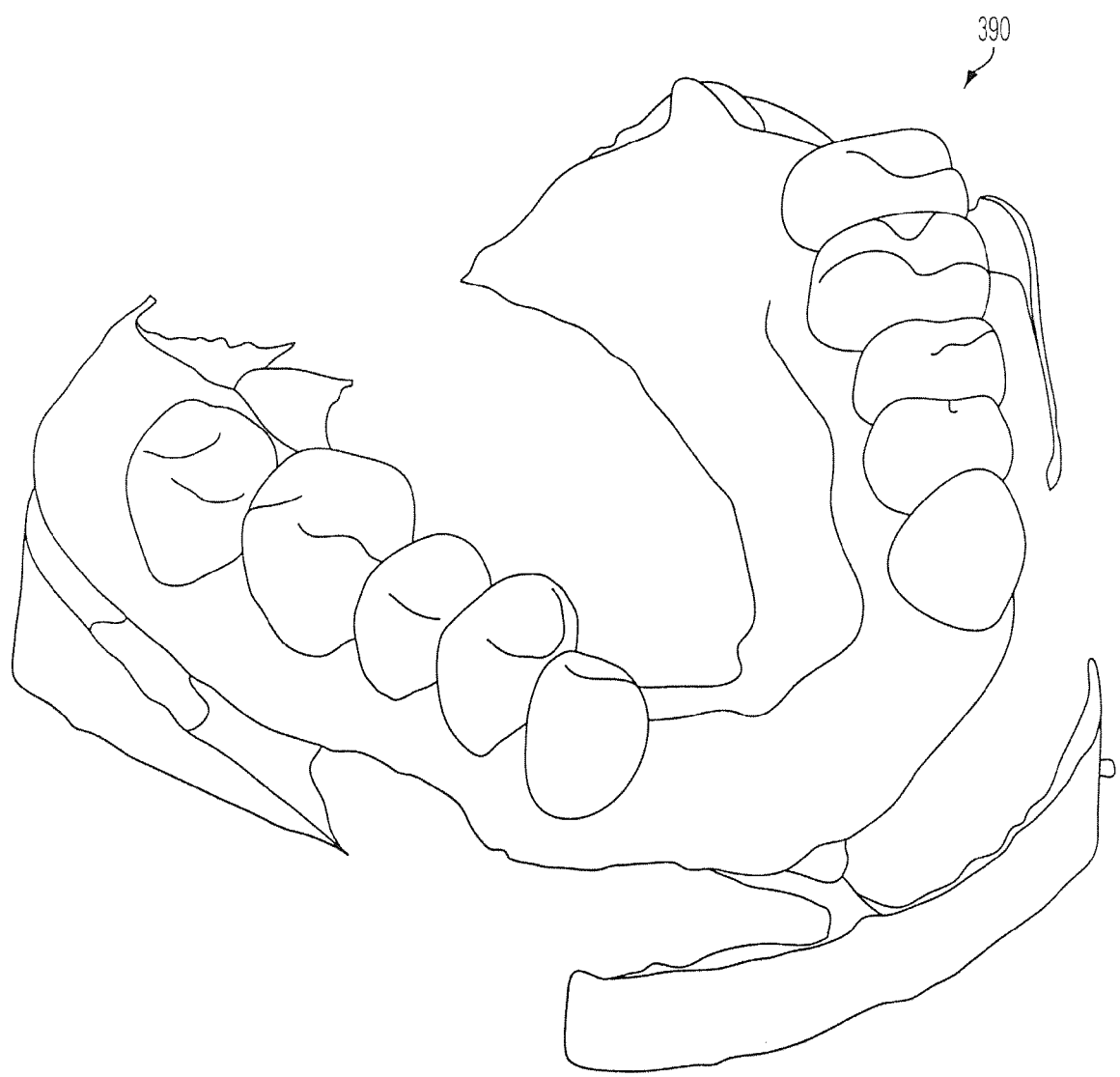
FIG. 3 is an illustration of a component of the embodiment described herein.

FIGS. 3-7 illustrate a specific exemplary implementation of the FIG. 2 technique. As mentioned above, the server receives a 3D digital data set of the patient's dentition (step 210), which in this example is a 3D geometric surface model 390 (FIG. 3). It should be appreciated that the received 3D geometric surface model 390 may be made and received from any suitable scanning means capable of capturing a cloud of data points representing features of the digital data set and can be formatted in a number of different data types such as "DICOM," "STL," "PLY," "IGES," "STEP," etc.

Such scanning typically requires the taking of a plurality of overlapping images that collectively span the patient's dentition to cover the dentition in its entirety. Various methods are known to recreate the entire model from these separate images. One such method uses precise information about the location of the model with respect to the camera to position and orient the plurality of images. In addition, commercially available three-dimensional image processing software also provides tools to combine discrete scans into a single 3D geometric surface model by matching the overlapping regions of the images. In a preferred embodiment, the patient's dentition is scanned using a three-dimensional scanner (typically collected as unordered ASCII text format; however any collection of three-dimensional point data is applicable) and created into a 3D digital data set, i.e., 3D geometric surface model or 3D volumetric model (preferably a "DICOM" file), using the imaging software to send to the server.

The server, if needed, can convert the received 3D geometric surface model into a 3D volumetric model of the patient's dentition. In alternative implementations, the server can directly receive a volumetric model of the patient's dentition and therefore does not need to create a volumetric model from a 3D geometric surface model.

Figure 4:
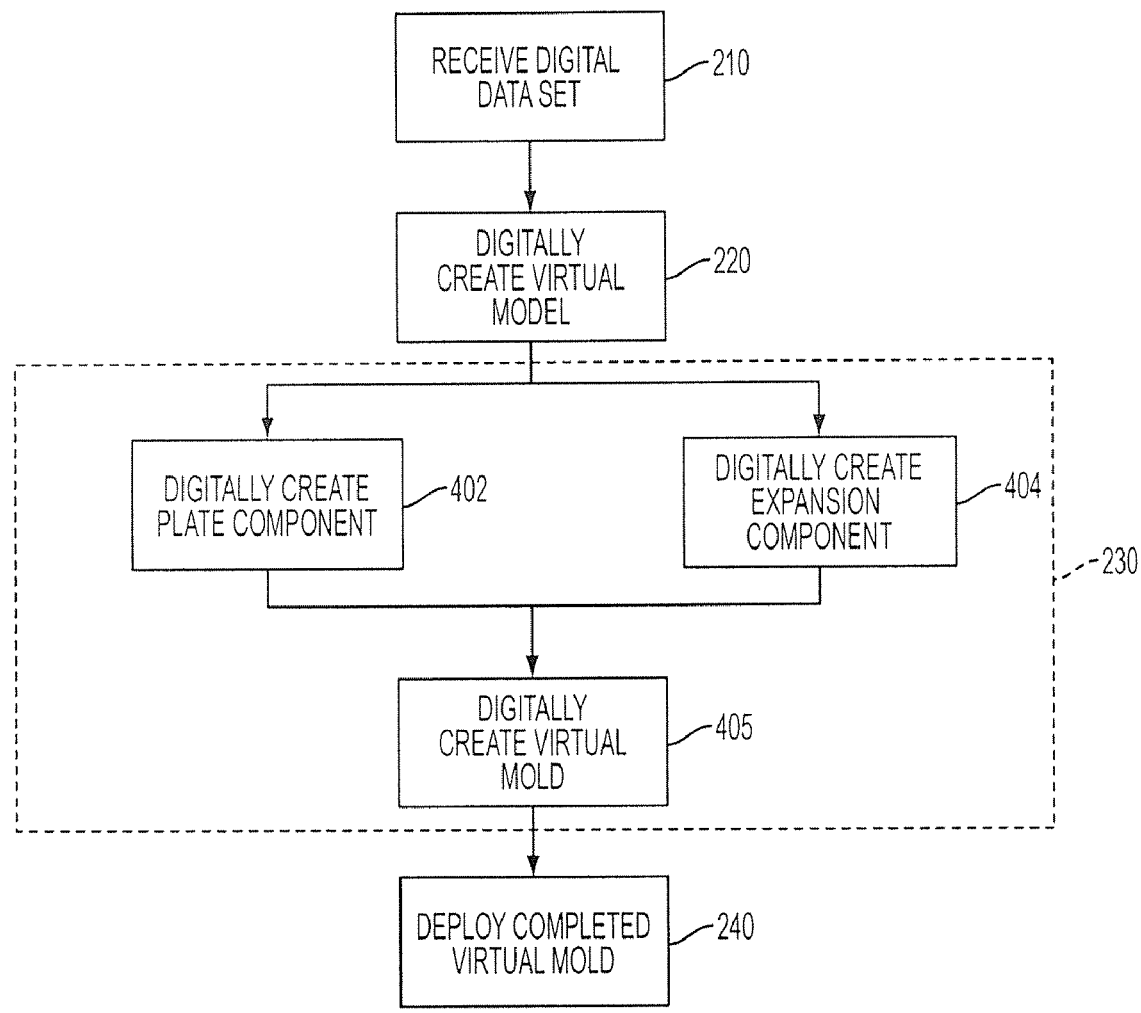
FIG. 4 is a flowchart of an embodiment described herein.

FIG. 4 illustrates an embodiment of the computer-implemented technique 400 for producing the virtual models. The server uses the received volumetric model to create the desired virtual model (step 220). This process of constructing a virtual model of the imaged patient's dentition and prosthesis can be rapidly executed in a fully automated process employing efficient computer code. Referring to FIG. 4, as described above, the server receives the 3D digital data set (step 210). Once the server receives the 3D digital data set, the server digitally creates a virtual model of the patient's dentition (step 220) and then digitally creates the virtual mold including components of a digital prosthesis (steps 402 and 404).

Figure 5:
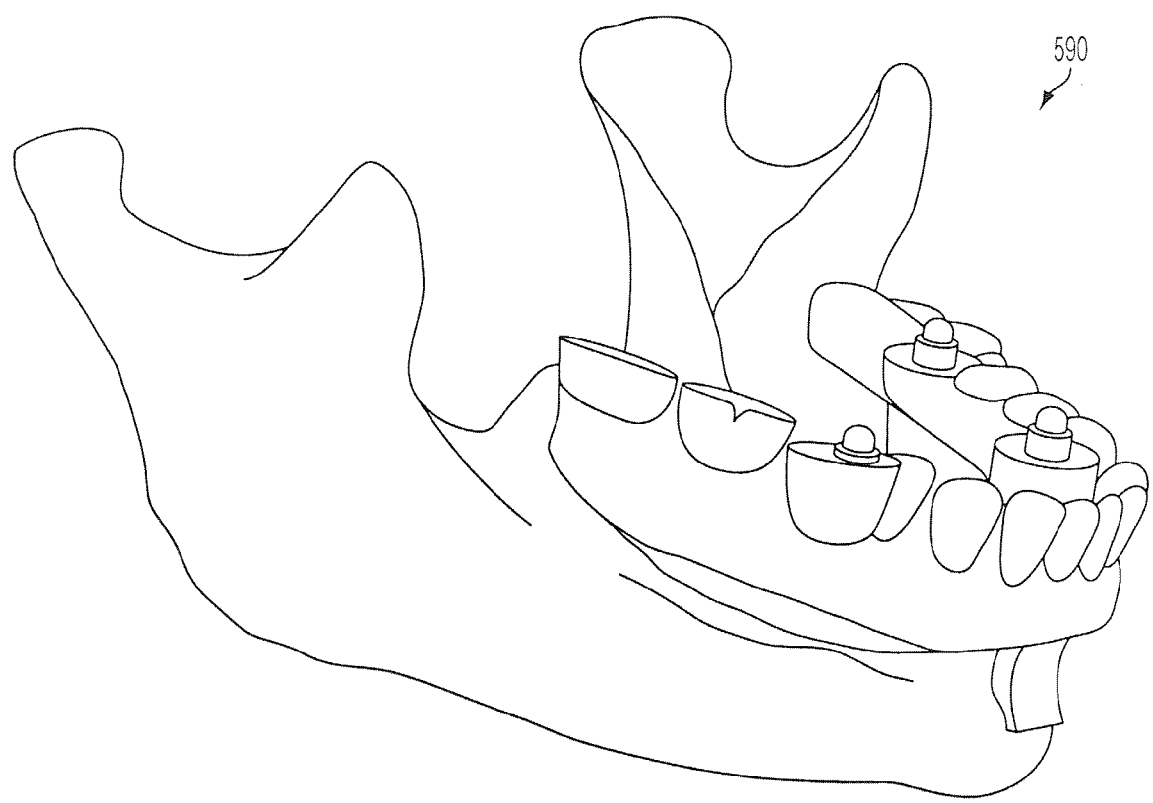
FIG. 5 is an illustration of a component of the embodiment described herein.

For example, if a user desires to create a prosthesis such as a bone distraction plate (an exemplary bone distraction plate is disclosed in U.S. Provisional Application No. 61/064,377, which is hereby incorporated by reference in its entirety), the user would submit a 3D digital data set as well as client specifications. Having received the 3D digital data set and the client specifications, a virtual model will be created (step 220). Then, using the client specifications, a plate component (step 402) and an expansion component (step 404) will be created. In step 402, a predetermined virtual pin and housing member is selected from a storage medium to comprise the plate component. The pin and housing member comprise standard mechanical pieces specifically designed for the bone distraction plate. In step 404, the expansion component is created. The expansion component is specifically designed and tailored to the patient's dentition. Then in step 405, the digital plate and extraction components are combined with the virtual model of the patient's dentition (step 220) to create a virtual mold 590 (FIG. 5). The virtual mold 590 serves as a three-dimensional blueprint for the rapid manufacturing of the prosthesis. In step 240, the completed virtual mold 590 is output to a rapid manufacturing device. The completed virtual mold 590 comprises slices, i.e., layers of a certain thickness (typically 0.1 to 0.25 mm), and their two-dimensional profiles are stored in a triangulated (tessellated) format such as, e.g., a ".STL" file.

Rapid manufacturing systems consist of a combination of a computer CAD system with an operation machine to perform the fabrication of a layer under computer control. The computer converts the received ".STL" data or other digital data sets to machine data, which is sent to an operation machine to generate each layer of the part, i.e., prosthesis, by the specific fabrication process. The process is repeated many times building the prosthesis, for example, layer by layer (additive manufacturing). The final step is finishing, removing the prosthesis from the machine, detaching support materials, and performing any necessary cleaning or surface finishing. Polishing, sealing, or painting the prosthesis can be used to improve its appearance. In some respects, additive manufacturing is related to subtractive manufacturing, in which a cutting machine such as a lathe or milling machine is controlled by computer to cut a specified shape, often with many different steps and cutting tool changes. In additive manufacturing, the fabrication process builds the prosthesis systematically by adding material instead of cutting it away, and a much wider range of shapes can be achieved, including cavities or intricate geometries that would be difficult or impossible to machine.

Figure 6:
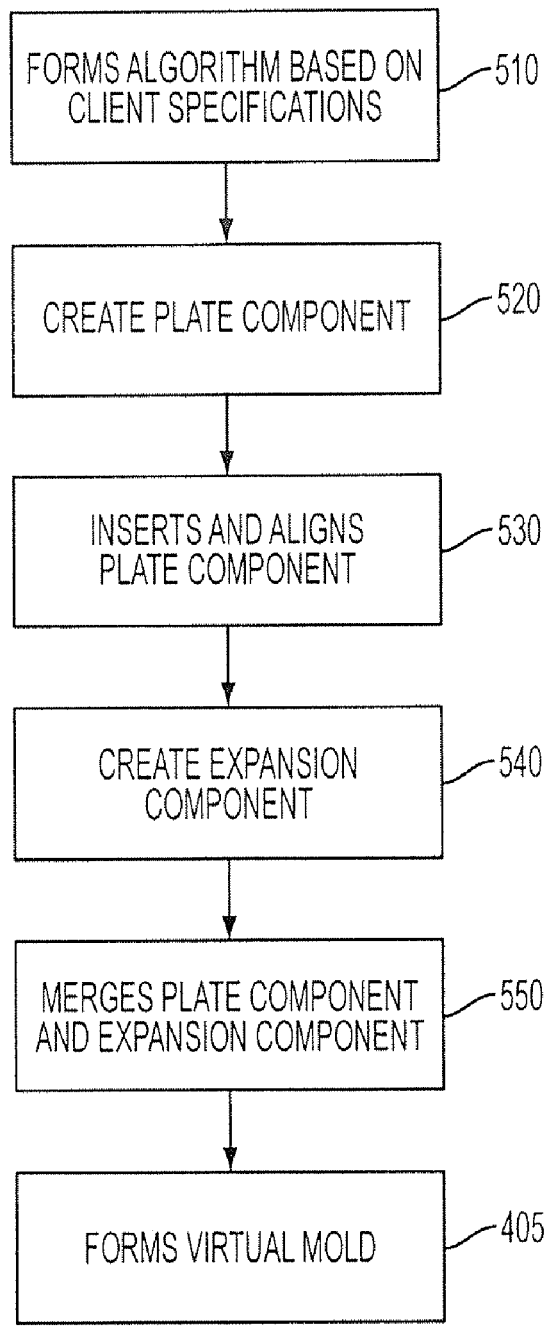
FIG. 6 is a flowchart of an embodiment described herein.

FIG. 6 illustrates a flowchart of the customized steps 230 conducted by the server. The customized steps 230 comprise the digital creation of the plate component and the expansion component (steps 402 and 404 shown in FIG. 4). Each of these steps are considered customized because each is based on the received client specifications. For example, in step 510, once a particular set of client specifications is considered, algorithms based on those client specifications are formed. Then, in step 520, using the formed algorithms, a plate component is created. In step 530, the plate component will be inserted and aligned. Then, in step 540, the expansion component is created and then in step 550 merged with the created plate component. Once the created plate component has been merged with the created expansion component, the 3D digital data set is combined to form the virtual mold 590 (step 405).

Figure 7:
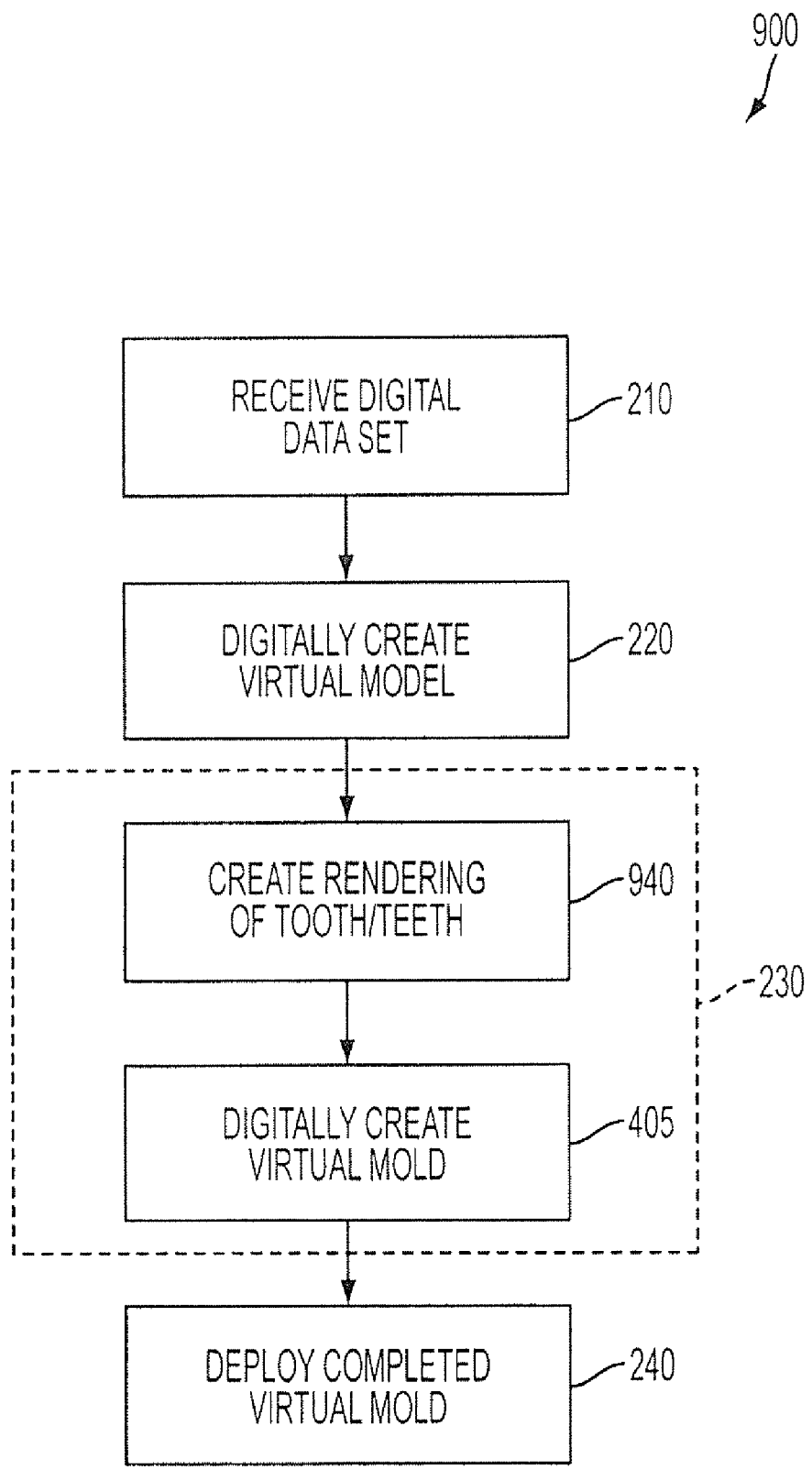
FIG. 7 is a flowchart of another embodiment described herein.

FIG. 7 illustrates another embodiment of the computer-implemented technique 900 for producing the virtual models. The server uses the received volumetric model and client specifications to create the desired virtual mold (steps 220 and 230). This process of constructing a virtual mold of the imaged patient's dentition and complete restoration can be rapidly executed in a fully automated process employing efficient computer code. As another example, if a user desires to create a complete restoration such as a crown or bridge, the user would submit a 3D digital set as well as client specifications.

Referring to FIG. 7, the server receives the 3D digital data set (step 210). Having received the 3D digital data set and client specifications, a virtual model is formed (step 220) and a rendering of each tooth will be created (step 940). The rendering of each tooth allows for the voxel processing and selective placement of dental materials to produce the entire genetic tooth form or forms from an original shape and position to a recreated shape and position. The virtual model is processed during step 940 to produce the thickness of the final restoration and, via a layering by voxel processing, a map of the desired dental materials (e.g., ceramic, acrylic, composite-polymers, etc.) to create a virtual mold including the desired shape, size, thickness and color.

Figure 8:
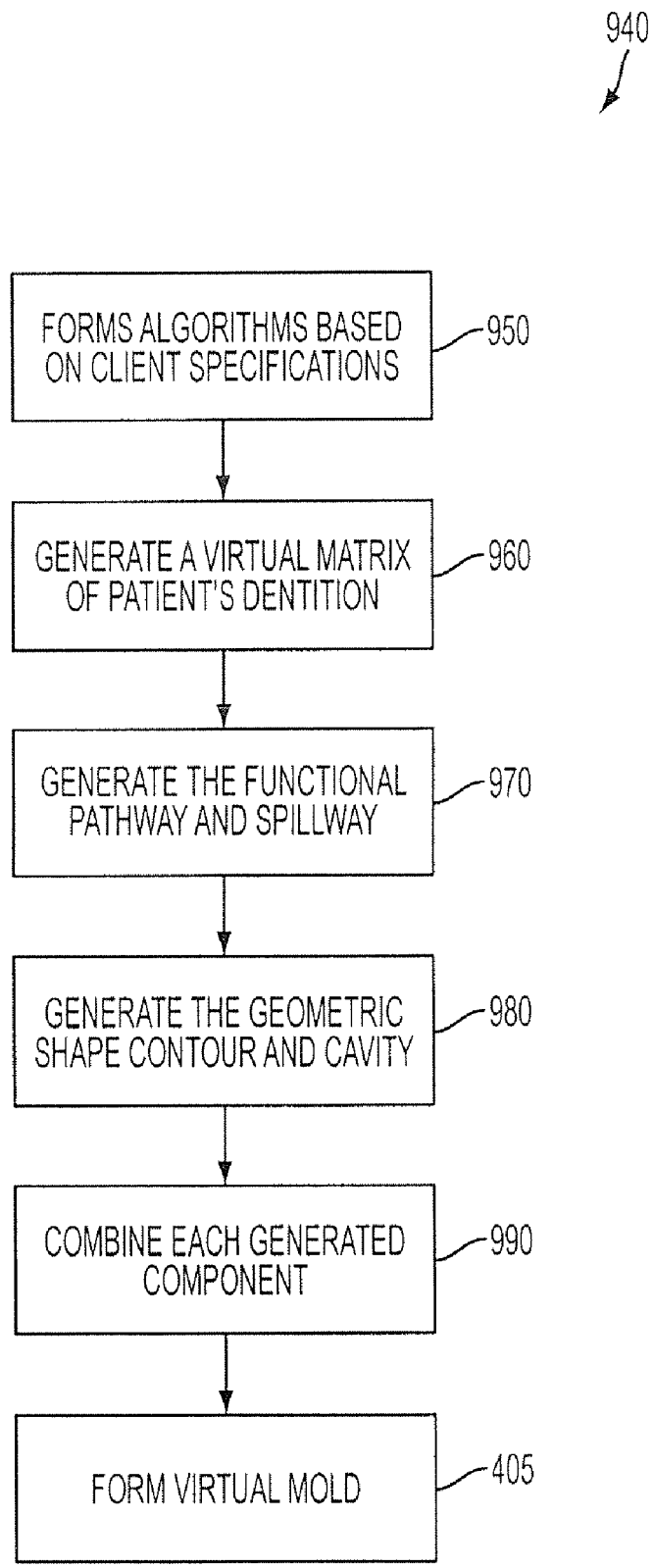
FIG. 8 is a flowchart of another embodiment described herein.
Figure 9:
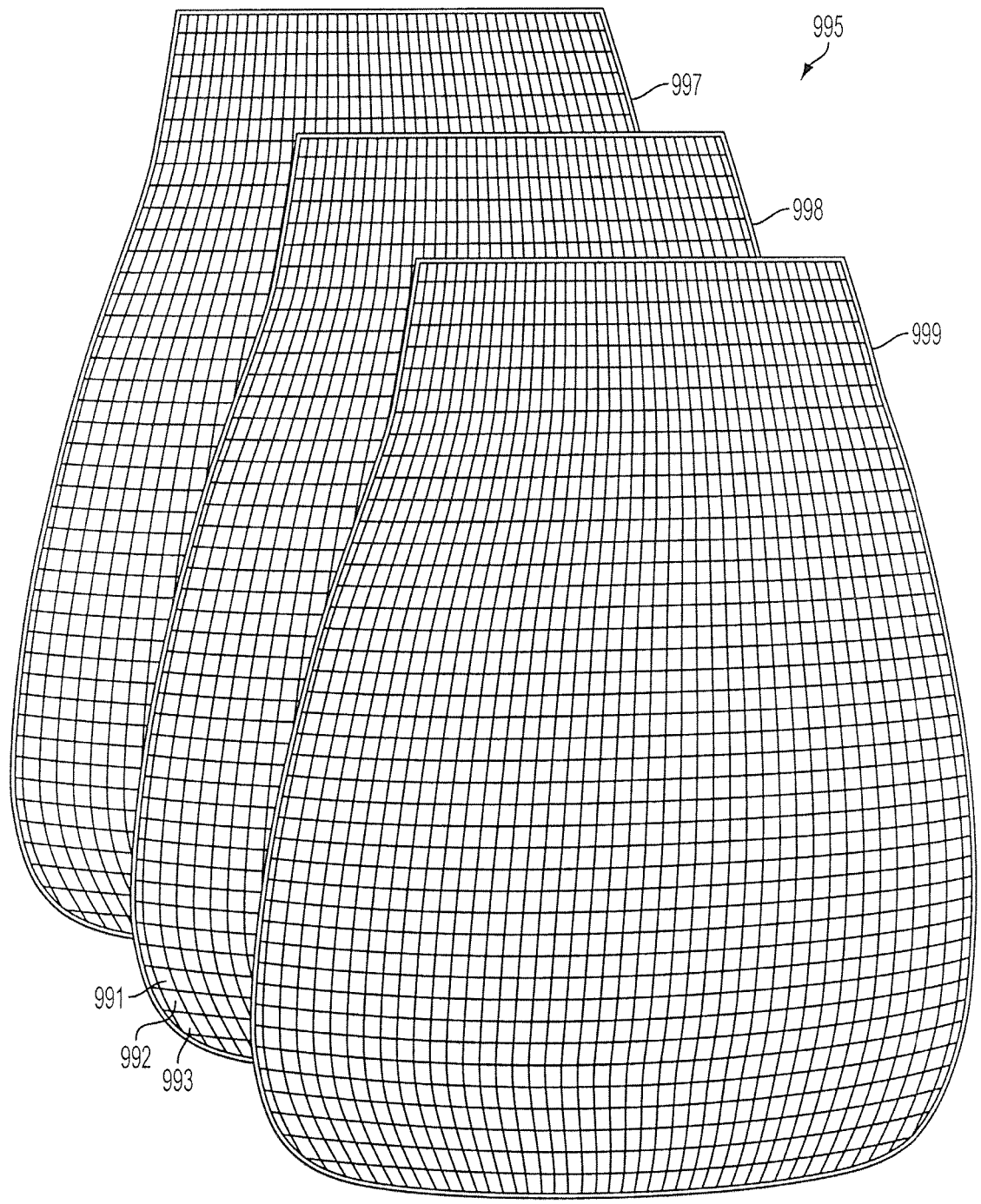
FIG. 9 is an illustration of a component of the embodiment described herein.

FIG. 8 illustrates a flowchart of step 940 conducted by the server. Once a particular set of client specifications is considered, algorithms based on those client specifications are formed (step 950). Then, in step 960, using the formed algorithms, a slice by slice (e.g., 997, 998, 999), pixel by pixel (e.g., 991, 992, 993, etc.) virtual matrix 995 of the patient's dentition is created (FIG. 9) having different kinds and colors of restorative material which correspond to each slice and/or pixel. It should be appreciated that the use of inter-pixel and inter-slice distance polychromatic coloring with different special effects allows for the virtual matrix to more accurately correspond to the natural patient's dentition. In step 970, the functional pathway for biting surfaces of articulation teeth and functional spillways for the escape of food materials during mastication are generated using the virtual model. Then, in step 980, using the various formed algorithms, the measurement height of contours for proper food deflection, the tooth to tooth relationship, the tooth to arch relationship, the arch to arch relationship, the arch size and tooth size ratios, the anterior and posterior tooth relationship, the occlusal contours, the facial contour, the buccal contour, the lingual contour, the mesial contour, the distal contour, the incisal contour, the incisal embrasure, the cervical embrasure, the buccal embrasure, and the lingual embrasure, among other things are calculated to generate the geometric shape contour and concavity produced during jaw movements. In step 990, the generated virtual matrix, the generated functional pathway and spillway, and the generated geometric shape contour and cavity are combined to create a rendered tooth/teeth.

Referring back to FIG. 7, the rendered tooth/teeth (step 940) is/are then combined with the virtual model of the patient's dentition (step 220) to form a virtual mold (step 405). The virtual mold 590 (FIG. 5) serves as a three-dimensional blueprint for the rapid manufacturing (described above) of the completed restoration. In step 240, the completed virtual mold 590 is deployed to a rapid manufacturing device. Similar to above, the completed virtual mold 590 comprises slices, i.e., layers of a certain thickness (typically 0.1 to 0.25 mm), and their two-dimensional profiles are stored in a triangulated (tessellated) format such as, e.g., a ".STL" file.

Figure 10:
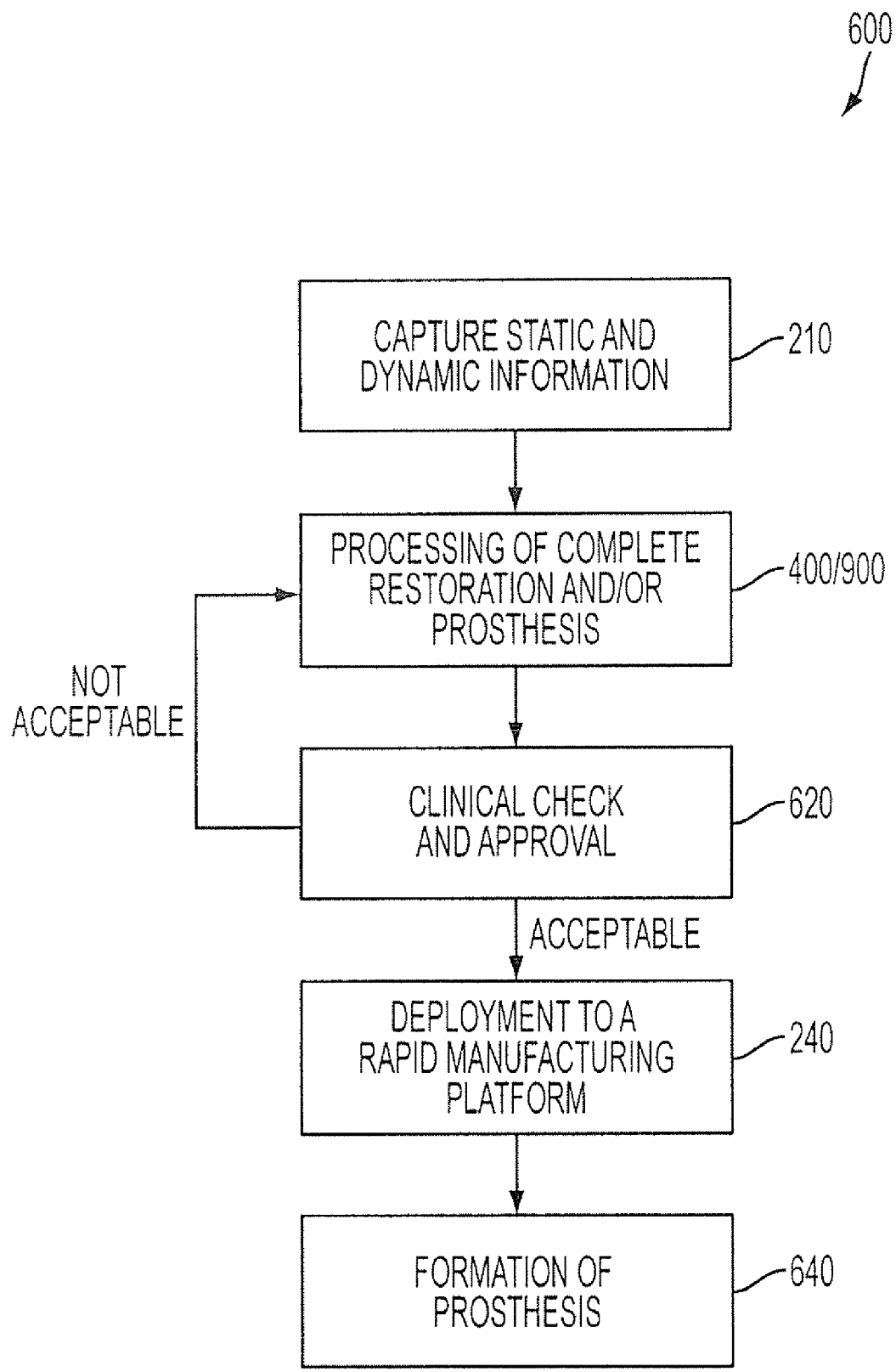
FIG. 10 is a flowchart of an embodiment described herein.

FIG. 10 illustrates an exemplary overall method 600 in which the exemplary computer-implemented techniques 400, 900 for producing the virtual molds 590 can operate. In step 210, as described above, 3D digital data 390 comprising static and/or dynamic information is captured. Then techniques 400, 900 (as described above) can be conducted to process the 3D digital data 390 to create a complete virtual restoration and/or prosthesis, i.e., the virtual mold 590. Once the virtual mold 590 is complete, it is checked by a clinician to determine whether or not it is accurately designed, in compliance with client specifications, and sufficient for the needed purpose. If so, the virtual mold 590 will be accepted. If it is not accepted, the method 600 will return to technique 400 or technique 900 to process the 3D digital data 390 and form another virtual mold. If the virtual mold 590 is acceptable, the method 600 will continue to step 240 where the virtual mold 590 is deployed to a rapid manufacturing platform. Once the virtual mold 590 has been deployed, the rapid manufacturing platform can form the prosthesis (step 640). It should be appreciated that any known rapid manufacturing platform or technique capable of forming a prosthesis using a virtual model as a blueprint can be used to form the prosthesis.

Figure 11:
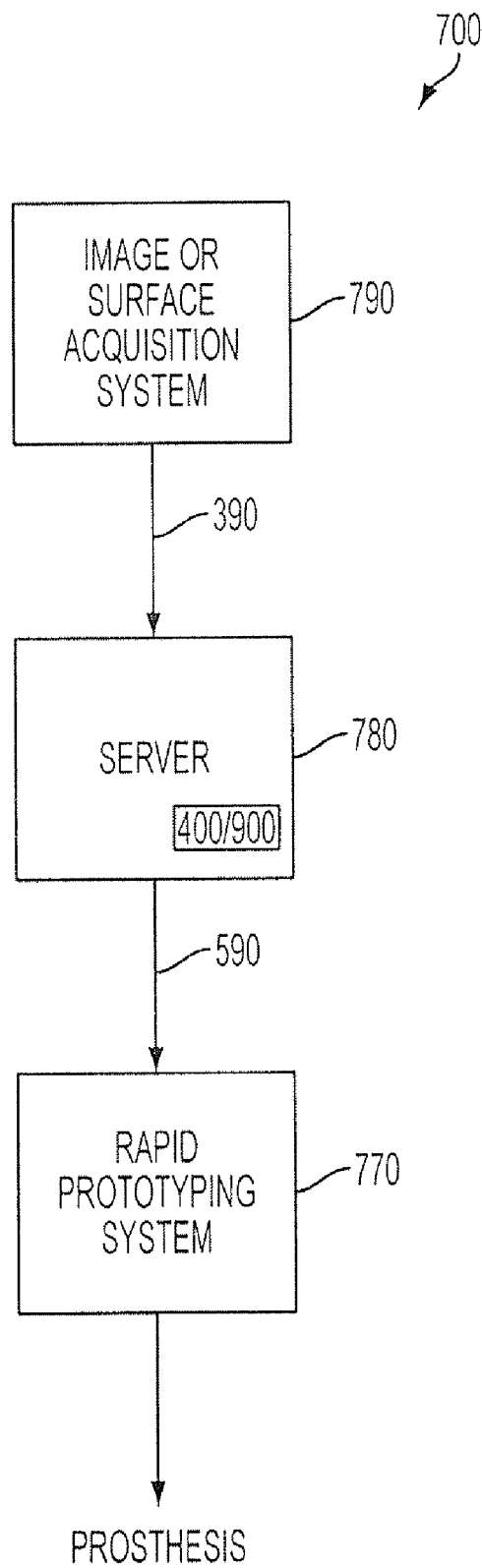
FIG. 11 is an illustration of an embodiment described herein.

FIG. 11 shows a system 700 used in producing a prostheses/complete restoration for dental appliances. The system 700 includes a processing unit, such as a programmed server 780, coupled to a producing system, such as a stereolithography machine or other rapid manufacturing system 770. The server 780 receives a 3D digital data set 390, such as a 3D geometric surface model or a volumetric image model, from an image or surface acquisition system 790, such as a laser scanning or destructive scanning device. The server 780 manipulates the 3D digital data set 390, using process(es) 400 and/or 900, to form a virtual mold 590, as described above, and delivers the virtual mold 590 to the rapid prototyping system 770.

It should be appreciated that there are no specific hardware requirements to use the described technique. Moreover, there are no special requirements for the type of computer or processor needed. The described technique can be implemented on any hardware and/or computer known in the art.

Figure 12:
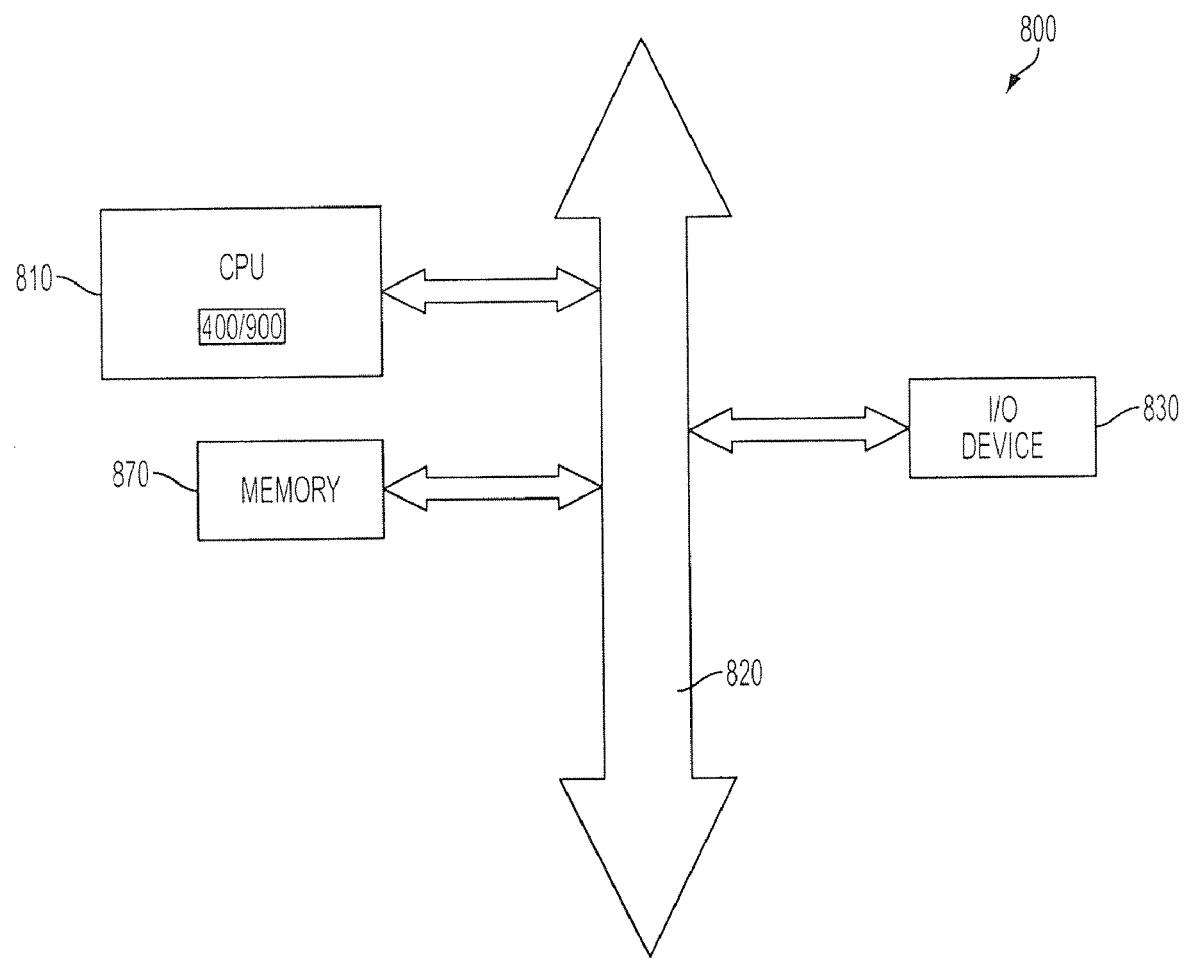
FIG. 12 is a processor system including an embodiment described herein.

FIG. 12 shows another system 800, a processor system modified to include the process for producing a virtual model. Examples of processor systems, which may employ the process for producing a prosthesis/complete restoration include, without limitation, computer systems, dental imaging systems, machine manufacturing systems, and others.

System 800 includes a central processing unit (CPU) 810 that executes process(es) 400 and/or 900, and which communicates with various other devices over a bus 820. Some of the devices connected to the bus 820 provide communication into and out of the system 800, illustratively including an input/output (I/O) device 830. Other devices connected to the bus 820 provide memory 870. While one input/output device 830 is shown, there may be multiple I/O devices such as a CD-ROM, hard drive, floppy disk, display, and keyboard as well as others. The process for producing a prosthesis/complete restoration may also be combined with a processor, such as memory, digital signal processor, or microprocessor, in a single integrated circuit.

Additionally, the embodiments described herein may be implemented as a software program stored on a computer readable storage medium (e.g., ROM) and executed by a processor. The computer readable information can be stored on a floppy disk, CD-ROM, ROM, RAM, DVD, HDD or any other suitable medium. It should also be appreciated that the embodiments are computer programmable by the user and/or other party as well as can be part of an internet browser.

Having described specific preferred embodiments of the invention with reference to the accompanying drawings, it is to be understood that the invention is not limited to those precise embodiments, and that various changes and modifications may be effected therein by one skilled in the art without departing from the scope or the spirit of the invention as defined in the appended claims.

Although the invention has been described in relation to a number of examples, in no way do those examples limit the invention. The invention can be applied to any system, industry or field that deals with three dimensional imagery. The invention can also be applied to any manufacturing system relating to dental applications. It should also be appreciated that the manner in which the 3D digital data set is obtained, or the type of equipment used to obtain the data is also not limited to the above described examples. It should also be appreciated that the manner in which the virtual model is deployed or outputted, or the type of equipment used to manufacture the virtual model is also not limited to the above described examples.

What is claimed as new and desired to be protected by Letters Patent of the United States is:

1. A method of forming a complete restoration comprising:
    capturing static and dynamic information of a patient's dentition;
    processing the static and dynamic information;
    creating a three-dimensional virtual model of the patient's dentition using the processed static and dynamic information;
    processing the virtual model to form a virtual mold, where forming the virtual mold includes forming a digital prosthesis;
    outputting the formed virtual mold to a rapid manufacturing platform; and
    constructing the digital prosthesis using the rapid manufacturing platform based on the virtual mold,
    wherein forming the digital prosthesis comprises:
        forming a plate component having a disc portion and a threaded cylinder portion extending vertically from the disc center of the portion for growing new bone by distraction osteogenesis in an area of deficient bone; and
        forming an expansion component having a hollow slot extending completely through and within the full length of the expansion component for operatively connecting and controllably retracting the plate component in a vertical direction.

2. The method of claim 1, wherein the step of capturing static and dynamic information comprises capturing a 3D geometric surface model.

3. The method of claim 1, wherein the step of capturing static and dynamic information comprises capturing a volumetric model.

4. The method of claim 1, further comprising: scanning a patient's dentition to form static and dynamic information.

5. The method of claim 1, wherein the digital prosthesis comprises a dental prosthesis and the step of processing the virtual model comprises: creating the plate component and the expansion component; and combining the virtual model and the created plate and expansion components to form the virtual mold.

6. The method of claim 5, wherein the step of creating the plate component comprises selecting a predetermined virtual pin and housing member.

7. The method of claim 1, wherein the step of forming a virtual mold comprises for a virtual bone distraction plate.

8. A system for forming a prosthesis comprising:
    an image acquisition system for receiving a digital data set representing a volumetric model of a patient's dentition;
    a server for processing the received digital data set and creating a virtual mold,
    wherein the virtual mold includes a prosthesis comprising:
        a plate component having a disc portion and a threaded cylinder portion extending vertically from the disc center of the portion for growing new bone by distraction osteogenesis in an area of deficient bone; and
        an expansion component having a hollow slot extending completely through and within the full length of the expansion component for operatively connecting and controllably retracting the plate component in a vertical direction; and
    a rapid manufacturing system for constructing the prosthesis using the formed virtual mold.

9. The system of claim 8, wherein the image acquisition system is a handheld intra-oral scanner.

10. The system of claim 8, wherein the image acquisition system is an X-ray machine.

11. The system of claim 8, wherein the server is a personal computer.

12. The system of claim 8, wherein the rapid manufacturing system is a stereolithography machine.

13. A system for producing a complete restoration comprising:
- a processor for capturing static and dynamic information of a patient's dentition, processing the static and dynamic information, creating a three-dimensional virtual model of the patient's dentition using the processed static and dynamic information, processing the virtual model to form a virtual mold, where forming the virtual mold includes forming a digital prosthesis, and outputting the formed virtual mold to a rapid manufacturing platform, wherein forming the digital prosthesis comprises: forming a plate component having a disc portion and a threaded cylinder portion extending vertically from the disc center of the portion for growing new bone by distraction osteogenesis in an area of deficient bone; and forming an expansion component having a hollow slot extending completely through and within the full length of the expansion component for operatively connecting and controllably retracting the plate component in a vertical direction; and
- a rapid manufacturing system for receiving the virtual mold from the processor and constructing the digital prosthesis based on the virtual mold.

14. A computer implemented method stored on a computer readable storage medium that when executed causes a computer to
- capture static and dynamic information of a patient's dentition;
- process the static and dynamic information;
- create a three-dimensional virtual model of the patient's dentition using the processed static and dynamic information;
- process the virtual model to form a virtual mold, where forming the virtual mold includes forming a digital prosthesis having a plate component having a disc portion and a threaded cylinder portion extending vertically from the disc center of the portion for growing new bone by distraction osteogenesis in an area of deficient bone; and an expansion component having a hollow slot extending completely through and within the full length of the expansion component for operatively connecting and controllably retracting the plate component in a vertical direction;
- output the formed virtual mold to a rapid manufacturing platform; and
- construct the digital prosthesis using the rapid manufacturing platform based on the virtual mold.

15. The method of claim 14, wherein the step of forming a virtual mold comprises forming a virtual bone distraction plate.

16. The method of claim 15, wherein the prosthesis is a dental prosthesis and the step of processing the received digital data set comprises:
- creating the plate component and the expansion component; and
- combining the received digital data set and the created plate and expansion components.

17. The method of claim 16, wherein the step of creating the plate component comprises selecting a predetermined virtual pin and housing member.

* * * * *